United States Patent [19]

Junino et al.

[11] Patent Number: 4,960,432
[45] Date of Patent: * Oct. 2, 1990

[54] META-PHENYLENEDIAMINES, PROCESS FOR PREPARATION THEREOF, INTERMEDIATE COMPOUNDS AND USE OF THESE META-PHENYLENEDIAMINES AS COUPLERS FOR THE OXIDATION DYEING OF KERATINOUS FIBRES AND ESPECIALLY HUMAN HAIR

[75] Inventors: Alex Junino, Livry-Gargan; Jean J. Vandenbossche, Aulnay-sous-Bois; Herve Borowiak, Tremblay-les-Gonesse; Gerard Lang, Saint-Gratien, all of France

[73] Assignee: L'Oreal, Paris, France

[*] Notice: The portion of the term of this patent subsequent to Sep. 12, 2006 has been disclaimed.

[21] Appl. No.: 200,170

[22] Filed: May 31, 1988

[30] Foreign Application Priority Data

May 29, 1987 [LU] Luxembourg .................... 86905

[51] Int. Cl.$^5$ ................ A61K 7/13; C07C 215/78; C07C 215/80
[52] U.S. Cl. ................................... 8/411; 8/408; 8/409; 8/412; 8/416; 8/421; 8/424; 564/443
[58] Field of Search ............. 564/443; 8/408, 409, 8/410, 411, 412, 424, 416, 421

[56] References Cited

U.S. PATENT DOCUMENTS

| 4,125,367 | 11/1978 | Bugaus et al. ............ 564/443 |
| 4,171,203 | 10/1979 | Rose et al. ............... 8/416 |
| 4,259,261 | 3/1981 | Bugaut et al. ............ 564/443 |
| 4,420,637 | 12/1983 | Bugaut et al. ............ 564/443 |
| 4,566,876 | 1/1986 | Brown et al. ............. 8/411 |
| 4,865,618 | 9/1989 | Junino et al. ............. 8/411 |
| 4,865,619 | 9/1989 | Junino et al. ............. 8/412 |

FOREIGN PATENT DOCUMENTS 0075242  3/1983  European Pat. Off. .

OTHER PUBLICATIONS

Chemical Abstracts, vol. 27, No. 4, Feb. 1933, p. 970, Baker et al.

*Primary Examiner*—Prince E. Willis
*Assistant Examiner*—Linda D. Skaling
*Attorney, Agent, or Firm*—Cushman, Darby & Cushman

[57] ABSTRACT

New meta-phenylenediamines, process for preparation thereof, intermediate compounds and use of these meta-phenylenediamines as couplers for the oxidation dyeing of keratinous fibres and especially human hair.

The invention relates to the compounds of the formula:

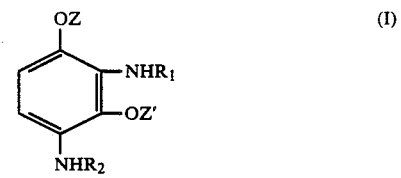

(I)

in which $R_1$ and $R_2$ denote, independently of one another, a hydrogen atom, a $C_1$–$C_4$ alkyl radical or a $C_2$–$C_3$ mono- or polyhydroxyalkyl radical, Z and Z' denote, independently of one another, a $C_1$–$C_4$ alkyl or $C_2$–$C_4$ hydroxyalkyl radical, with the proviso that, when $R_1$ and $R_2$ simultaneously denote a hydrogen atom, Z and Z' do not simultaneously denote a methyl radical, and to their addition salts with an acid, to a process for preparation thereof and also to their use, by way of couplers, in an aqueous vehicle, in combination with at least one oxidation dye percursor of the para type, for the dyeing of human hair.

The invention also relates to the intermediate compounds of the formula:

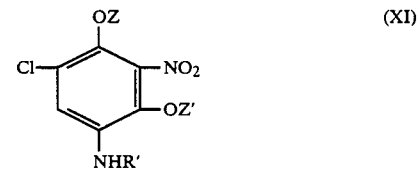

(XI)

in which R' denotes a hydrogen atom, a $C_1$–$C_4$ alkyl radical, a $C_2$ or $C_3$ mono- or polyhydroxyalkyl radical, or an acetyl or β-chloethoxycarbonyl radical, and z and z' denote, independently of one another, a $C_1$–$C_4$ alkyl radical.

17 Claims, No Drawings

META-PHENYLENEDIAMINES, PROCESS FOR PREPARATION THEREOF, INTERMEDIATE COMPOUNDS AND USE OF THESE META-PHENYLENEDIAMINES AS COUPLERS FOR THE OXIDATION DYEING OF KERATINOUS FIBRES AND ESPECIALLY HUMAN HAIR

The present invention relates to new meta-phenylenediamines, to a process for preparation thereof, to intermediate compounds, to dyeing compositions for keratinous fibres, and especially for human hair, containing these meta-phenylenediamines by way of couplers combined with oxidation dye precursors, and also to a dyeing process using the said compositions.

It is known that, for dyeing keratinous fibres such as human hair or furs, it is common to use dyeing compositions containing oxidation dye precursors, and especially para-phenylenediamines or ortho- or para-aminophenols, which are generally designated by the term oxidation bases.

It is known that, in order to vary the hues obtained with these oxidation bases, couplers or colouration modifiers, and especially meta-phenylenediamines, meta-aminophenols and meta-diphenols, are used.

In the oxidizing alkaline media normally used in oxidation dyeing, para-phenylenediamines and para-aminophenols give rise, in the presence of couplers such as meta-phenylenediamines, to coloured indamines or indoanilines.

The indamines formed from meta-phenylenediamines and from para-phenylenediamines in an oxidizing alkaline medium, and more especially in the presence of hydrogen peroxide, impart very strong blue colourations to keratinous fibres. The indoanilines formed from meta-phenylenediamines and from para-aminophenols in an oxidizing alkaline medium impart red colourations of more or less purple hue to keratinous fibres. Depending on the oxidation bases with which they are combined, meta-phenylenediamines can hence give red or blue colourations, these being two fundamental colours in hair dyeing, which are essential for obtaining not only blacks and greys but also copper-coloured or ashen chestnut colourations. The extremely important part played by meta-phenylenediamines in oxidation hair dyeing is thus evident.

It is important, moreover, that the oxidation bases and couplers which are used in oxidation dyeing compositions impart to the hair colourations which are stable to light, to washing, to inclement weather and to perspiration, and which show little or no selectivity. It is also necessary that these compounds possess the quality of good safety in use.

Many couplers of the type comprising meta-phenylenediamines substituted on the aromatic ring are already known. However, a large number of these do not meet the desired requirements.

The Applicant has just discovered new meta-phenylenediamines which combine very good safety in use with the dyeing qualities of a good coupler, and which can hence be advantageously used as couplers in combination with oxidation dye precursors, in particular of the para type, in oxidation dyeing compositions for keratinous fibres.

When combined with most para-phenylenediamines in an oxidizing alkaline medium, the meta-phenylenediamines according to the invention impart to the hair strong blue colourations which are more or less rich in green, or purples of more or less red hue.

When they are combined with para-aminophenols in an oxidizing alkaline medium, the meta-phenylenediamines according to the invention impart to the hair red colourations having good stability.

The subject of the present invention is hence the meta-phenylenediamines corresponding to the formula (I) below, or their addition salts with an acid:

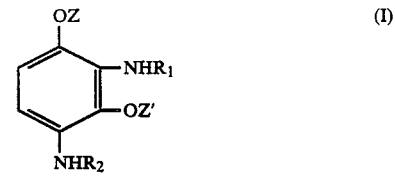

in which formula:

$R_1$ and $R_2$ denote, independently of one another, a hydrogen atom, an alkyl radical having 1 to 4 carbon atoms or a mono- or polyhydroxy alkyl radical having 2 or 3 carbon atoms; and Z and Z' denote, independently of one another, an alkyl radical having from 1 to 4 carbon atoms or a hydroxy alkyl radical having from 2 to 4 carbon atoms, with the proviso that, when $R_1$ and $R_2$ simultaneously denote a hydrogen atom, Z and Z' do not simultaneously denote a methyl radical.

The subject of the present invention is also a process for preparing the compounds of formula (I), and also the intermediate compounds of the following formula (XI):

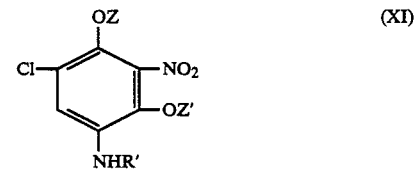

in which Z and Z' denote an alkyl radical having 1 to 4 carbon atoms or a hydroxy alkyl radical having 2 to 4 carbon atoms, and R' denotes a hydrogen atom, an alkyl radical having from 1 to 4 carbon atoms, a mono-or polyhydroxy alkyl radical having 2 or 3 carbon atoms or an acetyl or β-chloroethoxycarbonyl radical.

The present invention also relates to the use, by way of couplers, of the compounds of the formula (I) or their addition salts with an acid, in combination with oxidation dye precursors, for the dyeing of keratinous fibres and especially human hair.

Another subject of the present invention is hence a hair dyeing composition comprising, by way of a coupler, at least one compound of the formula (I) or one of its salts with acids, in combination with at least one oxidation dye precursor of the para type, in a cosmetically acceptable aqueous vehicle.

The present invention also relates to the process for dyeing hair using the above dyeing composition.

The compounds of the formula (I) are prepared from 2,4-disubstituted 3,5-dinitrochlorobenzenes of formula (II) below:

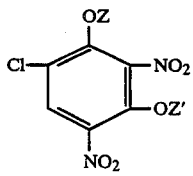

in which Z and Z' have the meanings stated above.

Depending on the meaning of the radicals $R_1$ and $R_2$ in the formula (I) of the final compounds, these compounds are prepared according to the following reaction schemes:

(1) Process for preparing the compounds (I) in which $R_1=R_2=H$ (compounds IA)

This process consists in reducing and dehalogenating, consecutively or simultaneously, the 2,4-disubstituted 3,5-dinitrochlorobenzenes of formula (II).

(a) Reduction of the compound (II) followed by a dehalogenation

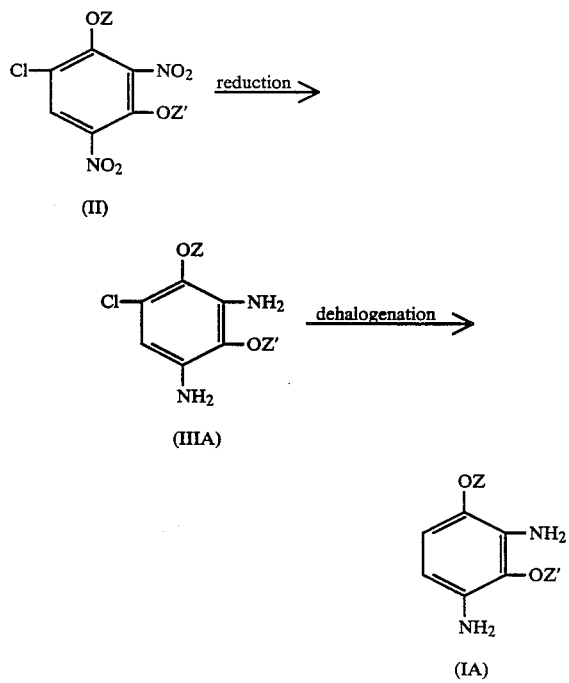

Z and Z' denote a $C_1$-$C_4$-alkyl or $C_2$-$C_4$-hydroxyalkyl radical, but not simultaneously a methyl radical.

The 2,4-disubstituted 3,5-dinitrochlorobenzene of the formula (II) is reduced with iron in the presence of acetic acid, at a temperature of between 50° and 100° C. A 2,4-disubstituted 3,5-diaminochlorobenzene of formula ($III_A$) is thereby obtained, and this is then subjected to a dehalogenation reaction. This reaction is performed in the presence of palladium on charcoal, ammonium acetate and triethylamine formate, in a solvent medium consisting of water, a lower alcohol or an aqueous-alcoholic mixture, at a temperature of between 50° and 100° C., according to Org. Chem., vol. 42, No. 22, 1977, p. 3491.

(b) Simultaneous reduction and dehalogenation of the compound (II)

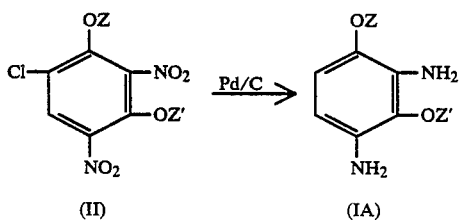

Z and Z' denote a $C_1$-$C_4$-alkyl or $C_2$-$C_4$-hydroxyalkyl radical, but do not simultaneously denote a methyl radical.

This reaction, by means of which the 1,3-disubstituted 2,4-diaminobenzene of the formula ($I_A$) may be obtained directly, is performed under hydrogen pressure in the presence of palladium on charcoal, as described in the article "Catalytic hydrogenation", Organic Synthesis, RYLANDER, Academic Press Inc. The addition of triethylamine or ammonium acetate favours the reaction. The latter is performed in a solvent consisting of water, a lower alcohol or an aqueous-alcoholic mixture, at a temperature of between 50° C. and 200° C.

(2) Process for preparing the compounds (I) in which $R_1=R_2=H$

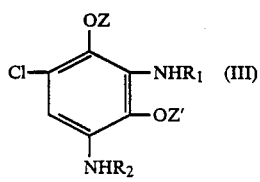

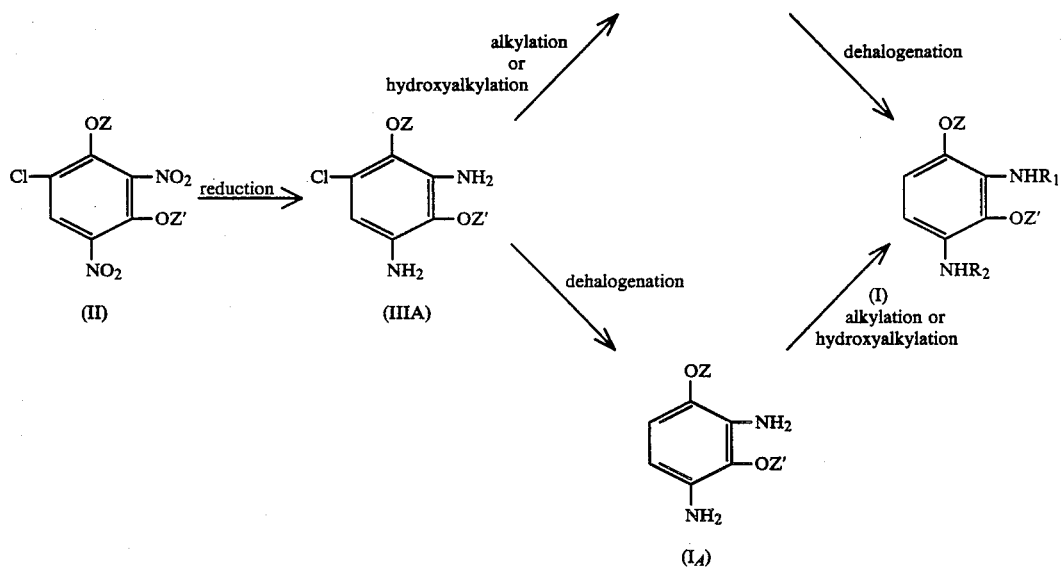

In the above formulae, $R_1$, $R_2$, Z and Z' have the meanings stated above, and Z and Z' can simultaneously denote a methyl radical.

The 2,4-disubstituted 3,5-dinitrochlorobenzene of the formula (II) is reduced with iron in the presence of acetic acid at a temperature of between 50° and 100° C. The 2,4-disubstituted 3,5-diaminochlorobenzene of the formula ($III_A$) is obtained.

According to a first reaction route, the compound ($III_A$) is dehalogenated as described above in (a) for the preparation of the compound ($I_A$). The amine groups of the 1,3-disubstituted 2,4-diaminobenzene of the formula ($I_A$) are then alkylated or hydroxylated according to the traditional processes for alkylation or hydroxyalkylation of aromatic amines.

The compound ($I_A$) may also be prepared by similtaneous reduction and dehalogenation according to the process (1) (b) described above.

According to a variant of the process, it is possible, in the first place, to perform the alkylation or hydroxyalkylation of the amine groups of the 2,4-disubstituted 3,5-diaminochlorobenzene of formula ($III_A$) to obtain the compound of the formula (III), which then undergoes a dehalogenation, according to the same process as that described above, to lead to the final 1,3-disubstituted 2,4-diaminobenzene of the formula (I).

(3) Process for preparing the compound (I) in which $R_1$=H and $R_2 \neq$H (compounds IB)

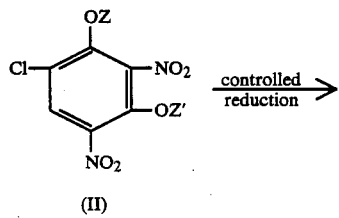

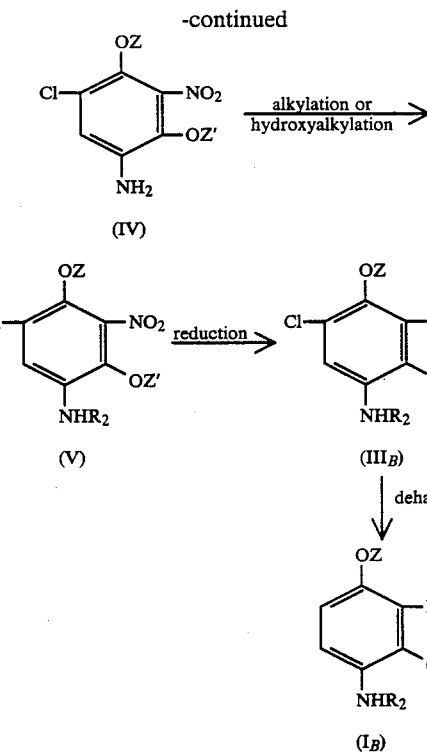

In the above formulae, Z, Z' and $R_2$ have the meanings stated above, it being possible for Z and Z' to denote simultaneously a methyl radical.

The 2,4-disubstituted 3,5-dinitrochlorobenzene of the formula (II) is subjected, in a first stage, to a controlled reduction which is accomplished by the transfer of hydrogen, in the presence of a catalyst such as palladium on charcoal and of cyclohexene used as a hydrogen donor.

In a second stage, the 2,4-disubstituted 5-amino-3-nitrochlorobenzene of the formula (IV) is subjected to an alkylation or a hydroxyalkylation of the amino group to lead to the compound (V), which is reduced in a third stage with iron in the presence of acetic acid at a temperature of between 20° and 100° C. The compound of the formula (III$_B$) is thereby obtained, and this is subjected in a fourth stage to a dehalogenation reaction, as described above for the preparation of the compounds (I$_A$).

(4) Process for preparing the compounds (I) in which R$_1$=H and R$_2$=H (compounds IC)

(a) First process the compound of the formula (II) as described in the process for preparing the compounds (I$_B$), is acetylated with acetic anhydride at a temperature of between 20° and 100° C. to lead to the compound of the formula (VI).

The compound (VI) is then simultaneously reduced and dehalogenated as described in the preparation process (b) for the compounds (I$_A$), under hydrogen pressure using palladium on charcoal, preferably in the presence of triethylamine or ammonium acetate.

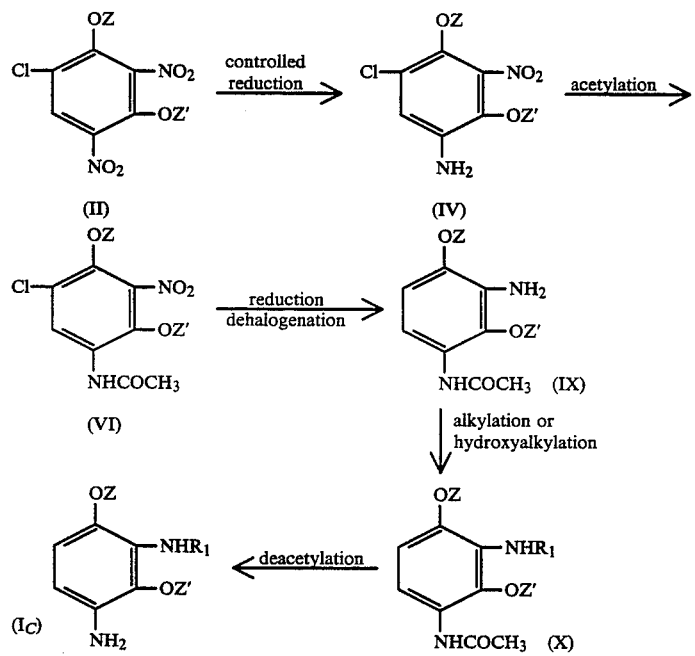

In the above formulae, Z, Z' and R$_1$ have the meanings stated above, it being possible for Z and Z' to denote simultaneously a methyl radical.

The 2,4-disubstituted 5-amino-3-nitrochlorobenzene of the formula (IV), obtained by controlled reduction of The compound (IX) thereby obtained is subjected to an alkylation or hydroxyalkylation to lead to the compound (X) which, after deacetylation, gives the compound (I$_C$).

(b) Second process

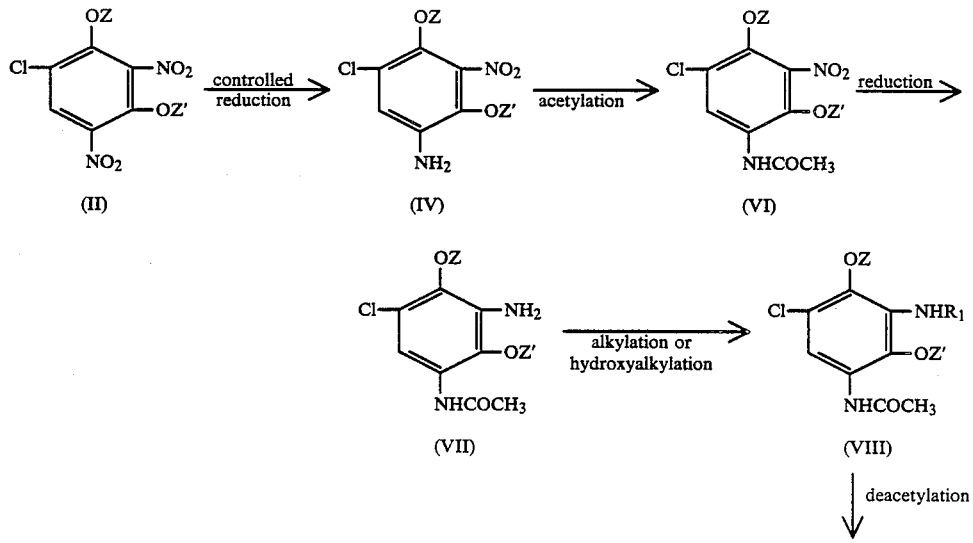

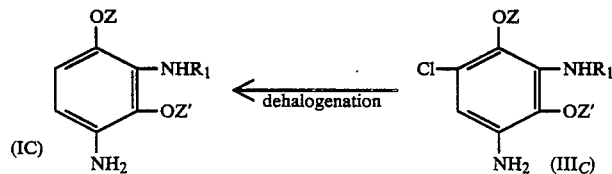

Z, Z' and $R_1$ having the meanings stated above, it being possible for Z and Z' to denote simultaneously a methyl radical.

The compound (VI), obtained in the first process by the controlled reduction of the compound (II) and acetylation of the compound (IV), undergoes reduction with iron in the presence of acetic acid at a temperature of between 50° and 100° C. to lead to the compound (VII).

The compound (VII) is alkylated or hydroxyalkylated to give the compound (VIII).

By deacetylation of the compound (VIII), the compound ($III_C$) is obtained, and this is dehalogenated as described in the process for preparing the compounds ($I_A$), in the presence of palladium on charcoal, ammonium acetate and triethylamine formate, in a solvent medium consisting of water, a lower alcohol or an aqueous-alcoholic mixture, at a temperature of between 50° and 100° C.

(5) Process for preparing the compounds (I) in which
$$R_1 \neq R_2 \neq H$$

These compounds, in which $R_1$ and $R_2$ do not denote a hydrogen atom and have different meanings, it hence being possible for Z and Z' to denote simultaneously a methyl radical, may be prepared by the alkylation or hydroxyalkylation of the primary amine groups of the compounds ($I_B$) or ($I_C$) according to traditional methods.

The alkylation and hydroxyalkylation stages involved in the different processes above are traditional reactions which are already known.

For the alkylation, it is possible to use alkyl halides or dialkyl sulphates.

For the hydroxyalkylation, the preferred method consists in reacting β-chloroethyl chloroformate with the compound bearing the amine group, and in converting the carbamate obtained to oxazolidone, which is then hydrolysed to lead to the hydroxyethyl derivative. This process is described in French patent application No. 2,571,364. The intermediate β-chloroethyl carbamate may also be subjected directly to the action of a strong inorganic base, such as sodium hydroxide or potassium hydroxide, to give the compound (I) in which $R_1$ or $R_2$ is a β-hydroxyethyl radical.

The starting compounds of the formula (II), namely the 2,4-disubstitued 3,5-dinitrochlorobenzenes, may be obtained according to one of the following three processes:

(a) First process

This process is described in "Recueil T. Chimiques, Pays Bas", R40, p. 451–471. It consists in nitrating 1,2,4-trichlorobenzene with fuming nitric acid, optionally in the presence of sulphuric acid, to obtain 1,2,4-trichloro-3,5-dinitrobenzene, of which the chlorine atoms at the 2- and 4-positions are then substituted by the radicals OZ and OZ' by reaction with the corresponding alkali metal alcoholate.

This process may be shown schematically in the following manner:

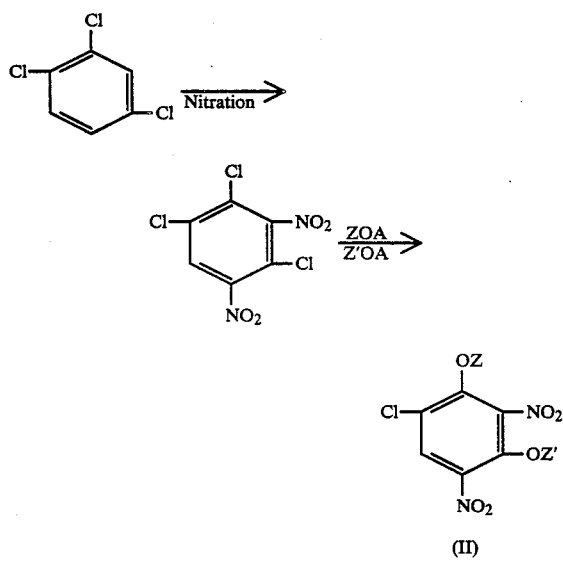

A being an alkali metal.

(b) Second process

This consists in nitrating the 2,4-dialkoxychlorobenzene or 2,4-bis(hydroxyalkoxy)chlorobenzene with fuming nitric acid, optionally in the presence of sulphuric acid. The 2,4-dialkoxy-3,5-dinitrochlorobenzene or 2,4-bis(hydroxyalkoxy)-3,5-dinitrochlorobenzene, respectively, is obtained in a single stage.

This process may be shown schematically in the following manner:

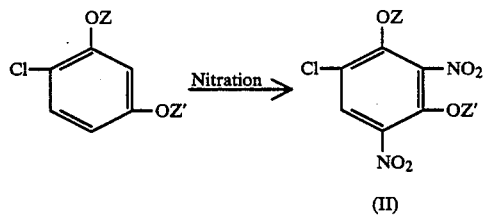

(c) Third process

This consists in alkylating or hydroxyalkylating 3,6-dichlorophenol or 3,4-dichlorophenol, then in nitrating the compound obtained and finally in substituting a chlorine atom by an alkoxy or hydroxyalkoxy radical by the action of an alkali metal alcoholate ZOA or Z'OA. This process is advantageous, in particular, in cases where Z and Z' are different.

This process may be summarized by the two schemes below:

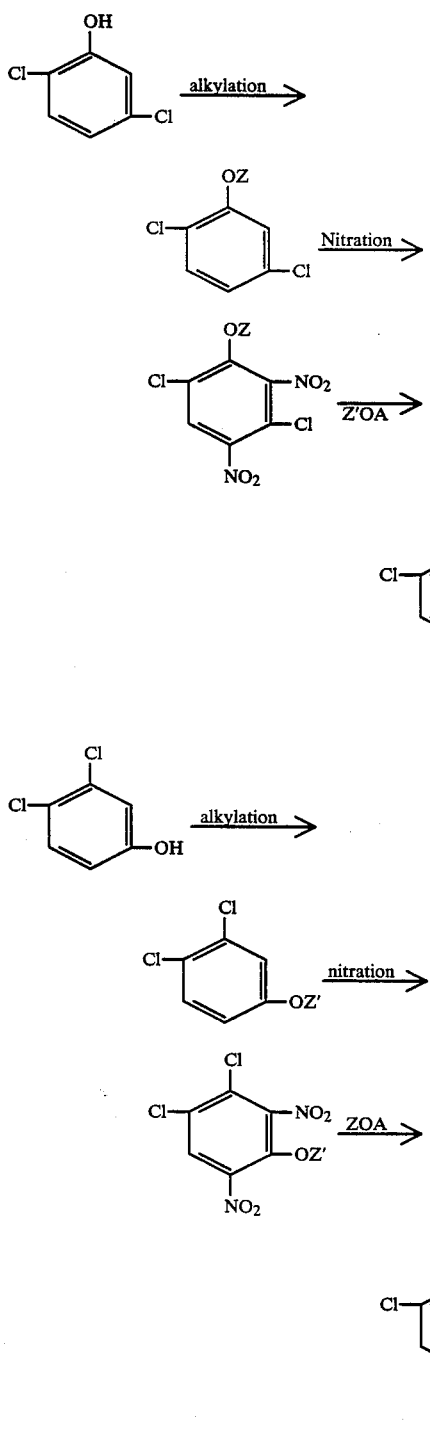

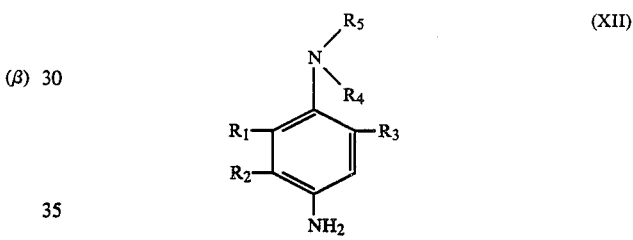

Compounds of formula (I) which are especially preferred according to the invention are 4-(β-hydroxyethyl)-amino-2-amino-1,3-dimethoxybenzene, 4-amino-2-(β-hydroxyethyl)amino-1,3-dimethoxybenzene, 4-methylamino-2-amino1,3-dimethoxybenzene, 2,4-bis(β-hydroxyethyl)amino-1,3-dimethoxybenzene, 2,4-diamino-1,3-diethoxybenzene and 2,4-diamino-1,3-bis(γ-hydroxypropoxy)benzene, as well as their addition salts with an acid and especially an inorganic acid such as hydrochloric acid, hydrobromic acid or sulphuric acid.

Intermediate compounds of the formula (XI) which are especially preferred according to the invention are 5-amino-2,4-dimethoxy-3-nitrochlorobenzene, 5-acetamido2,4-dimethoxy-3-nitrochlorobenzene, 5-methylamino-2,4-dimethoxy-3-nitrochlorobenzene and 5-(β-chloroethoxycarbonyl)amino-2,4-dimethoxy-3-nitrochlorobenzene.

The hair dyeing compositions according to the invention comprise, by way of a coupler, at least one compound of the formula (I) or one of its salts with an acid, in combination with at least one oxidation dye precursor of the para type, in a cosmetically acceptable aqueous vehicle.

The oxidation dye precursor of the para type is chosen from benzene derivatives and heterocyclic derivatives such as, for example, pyridine, to which derivatives two amino groups or one amino group and one hydroxy group are bound in the para position. These oxidation dye precursors may be present in the dyeing compositions in the form of free bases or in the form of addition salts with acids.

Especially preferred oxidation dye precursors which are usable according to the invention are chosen from the para-phenylenediamines corresponding to the following general formula (XII):

or the corresponding salts, in which formula $R_1$, $R_2$ and $R_3$ are identical or different and denote a hydrogen or halogen atom, an alkyl radical having 1 to 4 carbon atoms or an alkoxy radical having 1 to 4 carbon atoms, $R_4$ and $R_5$ are identical or different and denote a hydrogen atom or an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, the alkyl or alkoxy groups denoted by $R_4$ and $R_5$ having from 1 to 4 carbon atoms, or alternatively $R_4$ and $R_5$ can form, together with the nitrogen atom to which they are linked, a piperidino or morpholino heterocycle, with the proviso that $R_1$ or $R_3$ denotes a hydrogen atom when $R_4$ and $R_5$ do not denote a hydrogen atom.

Among the compounds of the formula (XII), there may be mentioned p-phenylenediamine, p-tolylenediamine, methoxy-para-phenylenediamine, chloro-para-phenylenediamine 2,6-dimethyl-p-phenylene-diamine, 2,5-dimethylpara-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-bis(β-hydroxy-ethyl)-para-phenylenediamine, 3-methyl-4-amino-N,N-bis(β-hydroxyethyl)aniline, 3-chloro-4-amino-N,N-bis(β-hydroxyethyl)aniline, 4-aminoN-ethyl-N-(carbamylmethyl)aniline, 3-methyl-4-amino-N-ethyl-N-(carbamylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morpholinoethyl)aniline, 3-methyl-4-amino-N- thyl-N-(β-morpholinoethyl)aniline, 4-amino-N-ethyl-N-(β-acetylaminoethyl)aniline, 4-amino-N-(β-methoxyethyl)aniline, 3-methyl-4-amino-N-ethyl-N-(β-acetylaminoethyl)aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(sulphoethyl)aniline, N-(4-aminophenyl)morpholine, N-(4-aminophenyl)piperidine, 2,3-dimethyl-p-phenylenediamine and isopropyl-p-phenylenediamine. These oxidation dye precursors of the para type may be introduced into the dyeing composition in the form of the free base or in the form of salts, such as in the form of a hydrochloride, hydrobromide or sulphate.

The compound (I) or its salts may also be used with p-aminophenols to give hues which are especially stable to light, to inclement weather and to washing, after development in the presence of an oxidizing agent. Among para-aminophenols, there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl)-4-aminophenol, 2-methoxy-4-aminophenol and 3-methoxy-4-aminophenol.

The compound (I) or its salts may also be used with heterocyclic para oxidation dye precursors, among which 2,5-diaminopyridine, 2-hydroxy-5-aminopyridine and tetraaminopyrimidine may be mentioned.

The dyeing compositions according to the invention can also contain oxidation dye precursors of the ortho type, such as ortho-aminophenols, ortho-phenylenediamines and ortho-diphenols. There may be mentioned, for example, 1-amino-2-hydroxybenzene, 6-methyl-1-hydroxy-2-aminobenzene and 4-methyl-1-amino-2-hydroxybenzene.

The dyeing compositions according to the invention containing the compound (I) or its salts can optionally contain other couplers which are known per se, such as meta-diphenols, meta-aminophenols, meta-phenylenediamines, meta-acylaminophenols, meta-ureidophenols, meta-carbalkoxyaminophenols, α-naphthol, and couplers possessing an active methylene group such as β-keto compounds and pyrazolones.

There may be mentioned, in particular, by way of example, 2,4-dihydroxyphenoxyethanol, 2,4-dihydroxyanisole, meta-aminophenol, resorcinol, resorcinol monomethyl ether, 2-methyl-5-aminophenol, 2-methyl-5-[N-(β-hydroxyethyl)-amino]phenol, 2-methyl-5-[N-(β-mesylaminoethyl)amino]phenol, 2,6-dimethyl-3-aminophenol, 6-hydroxybenzomorpholine, 2,4-diaminophenoxyethanol, 6-aminobenzomorpholine, 2-[N-(β-hydroxyethyl)amino]-4-aminophenoxyethanol, 2-amino-4-[N-(β-hydroxyethyl)amino]anisole, 2,4-diaminophenylβ,γ-dihydroxypropyl ether, 2,4-diaminophenoxyethylamine, 3,4-methylenedioxyphenol and 3,4-methylenedioxyaniline, and their salts.

As is well known, it is possible to add to these compositions, for the purpose of altering the hue or enriching with glints the colourations provided by the oxidation dye precursors, direct dyes such as azo or anthraquinone dyes or nitro derivatives of the benzene series.

The para compounds and the couplers used in the dyeing compositions according to the invention preferably represent collectively from 0.1 to 7% of the total weight of the said composition. The concentration of the compound (I) can vary between 0.05 and 3.5% of the total weight of the composition.

The cosmetically acceptable aqueous vehicle has a pH which can vary between 8 and 11, and it is preferably between 9 and 11.

It is adjusted to the desired value by means of an alkalinizing agent such as ammonia solution, alkali metal carbonates or alkanolamines such as mono-, di- or triethanolamine.

The dyeing compositions according to the invention, in their preferred embodiment, also contain anionic, cationic, nonionic or amphoteric surfactants, or mixtures thereof. Among these surfactants, there may be mentioned, more especially, alkylbenzenesulphonates, alkylnaphthalenesulphonates, fatty alcohol sulphates, ether sulphates and sulphonates, quaternary ammonium salts such as trimethylcetylammonium bromide and cetylpyridinium bromide, fatty acid ethanolamides, optionally oxyethylenated, polyoxyethylenated acids, alcohols and amines, polyglycerolated alcohols, polyoxyethylenated or polyglycerolated alkylphenols and also polyoxyethylenated alkyl sulphates. The surfactants are present in the compositions according to the invention in proportions of between 0.5 to 40% by weight, and preferably between 4 and 30% by weight, relative to the total weight of the composition.

These compositions can also contain organic solvents for solubilizing any compounds which are insufficiently soluble in water. Among these solvents, there may be mentioned, by way of example, $C_1$–$C_4$ lower alkanols such as ethanol and isopropanol; glycerol; glycols or glycol ethers such as 2-butoxyethanol, ethylene glycol, propylene glycol, diethylene glycol monoethyl ether and monomethyl ether; and also similar products, and mixtures thereof. The solvents are preferably present in a proportion of between 1 and 40% by weight, and especially between 5 and 30% by weight, relative to the total weight of the composition.

The thickening agents which can be added to the compositions according to the invention are selected, in particular, from the group composed of sodium alginate, gum arabic, cellulose derivatives such as methylcellulose, hydroxyethylcellulose, hydroxypropylcellulose, hydroxymethylcellulose and carboxymethylcellulose, acrylic acid polymers and xanthan gum. It is also possible to use inorganic thickening agents such as bentonite. These thickening agents are preferably present in proportions of between 0.1 to 5% by weight, and especially between 0.5 and 3% by weight, relative to the total weight of the composition.

The compositions can contain antioxidant agents chosen, in particular, from sodium sulphite, thioglycolic acid, sodium bisulphite, ascorbic acid and hydroquinone. These antioxidant agents are present in the composition in proportions of between 0.05 and 1.5% by weight, relative to the total weight of the composition.

Other adjuvants which are usable according to the invention are, for example, penetrating agents, sequestering agents, buffers and perfumes.

The dyeing compositions according to the invention may be presented in various forms, such as in the form of liquids, creams or gels, or in any other form suitable for carrying out a dyeing of keratinous fibres, and in particular human hair. They can also be packaged in aerosol cans in the presence of a propellent agent.

The dyeing compositions according to the invention, containing an oxidation dye precursor of the para type and the compound (I) or one of its salts, are used in a hair dyeing process employing development with an oxidizing agent.

According to this process, the dyeing composition described above is mixed at the time of use with a sufficient quantity of an oxidizing solution, and the mixture obtained is then applied on the hair.

The oxidizing solution contains oxidizing agents such as hydrogen peroxide, urea peroxide or persalts such as ammonium persulphate. A "20 volumes" hydrogen peroxide solution is preferably used.

The mixture obtained is applied on the hair and left in place for 10 to 40 minutes, and preferably 15 to 30 minutes, after which the hair is rinsed, washed with shampoo, rinsed again and dried.

Another process employing the compound (I) according to the invention consists in dyeing the hair in accordance with a multi-stage process, according to which, in a first stage, the para oxidation dye precursor is applied by means of a composition defined above, and, in a second stage, compound (I) is applied. The oxidizing agent is present in the composition applied in the second stage, or is alternatively applied on the hair itself in a third stage, the conditions of exposure, drying and washing being identical.

The examples below serve to give a better illustration of the invention, but under no circumstances limit the scope of the latter.

EXAMPLE OF PREPARATION NO. 1

Preparation of 4-(β-hydroxyethyl)amino-2-amino-1,3-dimethoxybenzene (compound IB)

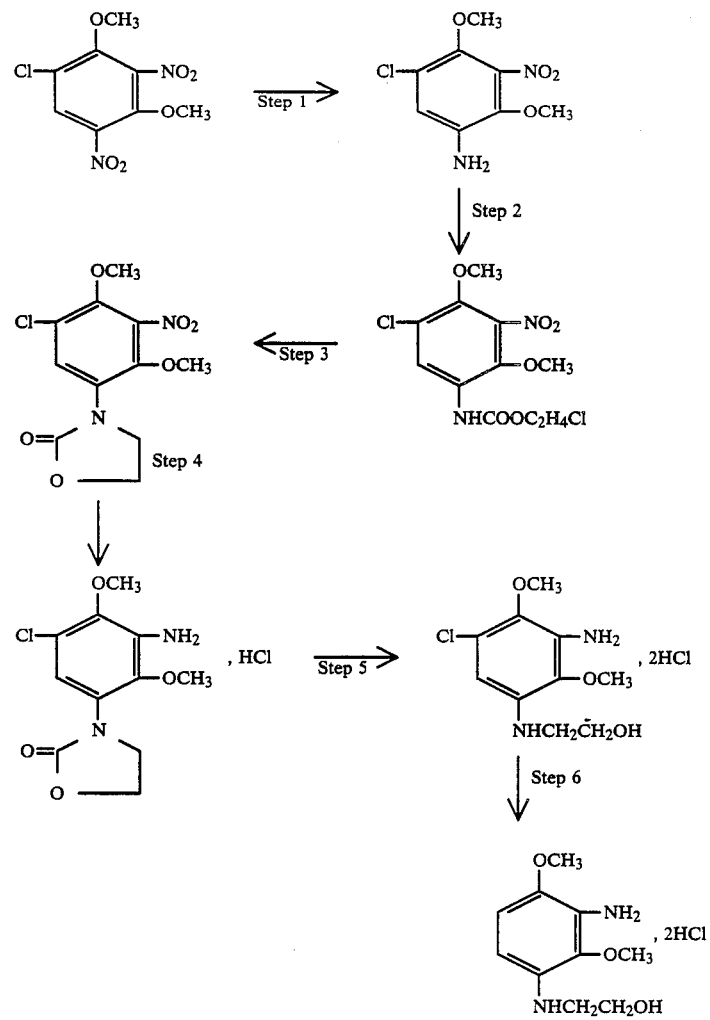

Step 1

Preparation of 5-amino-2,4-dimethoxy-3-nitrochlorobenzene

A mixture consisting of 0.2 mole (52.5 g) of 3,5-dinitro-2,4-dimethoxychlorobenzene and 15.9 g of palladium on charcoal (10%) in 260 ml of absolute ethanol containing 110 ml of cyclohexene was heated to reflux for 1 hour.

The catalyst was removed by filtration. An oil was obtained after evaporation to dryness under vacuum, which crystallized after an addition of iced water. After thorough draining and drying, the product obtained was recrystallized from a benzene and cyclohexane mixture. It melted at 68° C.

The elemental analysis of the product obtained was as follows:

|  | Calculated for $C_8H_9N_2O_4Cl$ | Found |
|---|---|---|
| C % | 41.28 | 41.10 |
| H % | 3.87 | 3.90 |

-continued

| | Calculated for C$_8$H$_9$N$_2$O$_4$Cl | Found |
|---|---|---|
| N % | 12.04 | 11.98 |
| O % | 27.52 | 27.68 |
| Cl % | 15.27 | 14.99 |

Step 2

Preparation of
5-(β-chloroethoxycarbonyl)amino-2,4-dimethoxy-3-nitrochlorobenzene 0.05 mole (11.7 g) of 5-amino-2,4-dimethoxy-3-nitrochlorobenzene was dissolved in 50 ml of dioxane. 5 g of calcium carbonate were added, then the temperature was raised to the region of 90° C. 0.05 mole (7.2 g) of β-chloroethyl chloroformate was then introduced with stirring. Upon completion of the addition, stirring was maintained for 30 additional minutes at 90° C. The inorganic salts present in the reaction mixture were removed by filtration while hot. After addition of iced water to the filtrate, the expected product crystallized. The product obtained was thoroughly drained and washed with water. After drying, it was recrystallized from ethanol. It melted at 93° C.

The elemental analysis of the product obtained was as follows:

| | Calculated for C$_{11}$H$_{12}$Cl$_2$N$_2$O$_6$ | Found |
|---|---|---|
| C % | 38.94 | 38.78 |
| H % | 3.54 | 3.53 |
| N % | 8.26 | 8.35 |
| O % | 28.32 | 28.40 |
| Cl % | 20.94 | 21.03 |

Step 3

Preparation of
N-[(3'-chloro-4',6'-dimethoxy-5'-nitro)phenyl]-1,3-oxazolidine-2-one 0.03 mole (10.2 g) of β-chloroethyl carbamate obtained according to the operating procedure described in step 2 was heated to 70° C. in 50 ml of methanol. 0.03 mole of sodium methylate as a 30% solution in methanol was added rapidly. Heating was maintained for 15 additional minutes upon completion of the addition. The inorganic salts were removed by filtration. From the filtrate which was cooled and diluted with iced water, the expected product which had crystallized was isolated by filtration. After drying, it was recrystallized from ethanol. It melted at 133° C.

The elemental analysis of the product obtained was as follows:

| | Calculated for C$_{11}$H$_{11}$ClN$_2$O$_6$ | Found |
|---|---|---|
| C % | 43.64 | 43.81 |
| H % | 3.64 | 3.64 |
| N % | 9.26 | 9.37 |
| O % | 31.74 | 31.62 |
| Cl % | 11.74 | 11.74 |

Step 4

Preparation of
N-[(3'-chloro-4',6'-dimethoxy-5'-amino)phenyl]-1,3-oxazolidine-2-one hydrochloride 12 g of powdered iron which had been reduced with hydrogen were added to 60 ml of water containing 3 ml of acetic acid and which had been previously heated in a boiling water bath, and 0.02 mole (6.05 g) of 1,3-oxazolidine-2-one obtained according to the operating procedure described in the previous step was added gradually with stirring. Upon completion of the additions, heating was maintained for 15 additional minutes. The iron slurries were removed from the reaction mixture by filtration while hot. The reaction mixture freed from the iron slurries was extracted with ethyl acetate. The ethyl acetate phase was washed with water and dried over sodium sulphate. The expected product was precipitated by addition of a 7N hydrochloric acid solution in absolute ethanol.

The elemental analysis of the product obtained was as follows:

| | Calculated for C$_{11}$H$_{14}$N$_2$O$_4$Cl$_2$ | Found |
|---|---|---|
| C % | 42.72 | 42.59 |
| H % | 4.53 | 4.64 |
| N % | 9.06 | 8.96 |
| O % | 20.71 | 20.60 |
| Cl % | 22.98 | 22.87 |

Step 5

Preparation of
5-(β-hydroxyethyl)amino-3-amino-2,4-dimethoxychlorobenzene hydrochloride 0.03 mole (9.3 g) of N-[(3'-chloro-4'-6'-dimethoxy-5'-amino)phenyl]-1,3-oxazolidine-2-one hydrochloride obtained according to the operating procedure described in the previous step was added to 10 ml of water containing 10 ml of ethanol. 18 ml of 10N sodium hydroxide were added to this solution. The mixture was heated for 30 minutes at 80° C. After cooling and phase separation, the upper phase was diluted with ethyl acetate. After washing with water and drying over sodium sulphate, 14 ml of a 7N hydrochloric acid solution in absolute ethanol were added. The expected product precipitated. It was recrystallized from a aqueous-alcoholic solution of hydrochloric acid.

The elemental analysis of the product obtained was as follows:

| Analysis | Calculated for C$_{10}$H$_{17}$N$_2$O$_3$Cl$_3$ | Found |
|---|---|---|
| C % | 37.56 | 37.44 |
| H % | 5.52 | 5.24 |
| N % | 8.76 | 8.83 |
| O % | 15.02 | 15.21 |
| Cl % | 33.33 | 33.07 |

Step 6

Preparation of
4-β-hydroxyethyl)amino-2-amino-1,3-dimethoxybenzene hydrochloride The mixture consisting of 37.2 g of ammonium acetate, 33 g of 10% palladium on charcoal, 0.12 mole (38.5 g) of 5-(β-hydroxyethyl)amino-3-amino-2,4-dimethoxychlorobenzene hydrochloride obtained according to the operating procedure described in step 5 was heated with stirring under reflux, in 240 ml of ethanol containing 24 ml of water. 36.4 ml of triethylamine were added, and then 15.5 g of formic acid were added dropwise. Heating was maintained for 30 minutes upon completion of the addition. The catalyst was removed by filtration while hot. The solids content obtained by evaporation of the filtrate under vacuum was dissolved in ethyl acetate. 52 ml of a 7N hydrochloric acid solution in absolute ethanol were added to the ethyl acetate, which had been dried over sodium sulphate, in order to precipitate the expected product. The product was recrystallized while hot from an aqueous-alcoholic solution of hydrochloric acid.

The analysis of the product obtained was as follows:

|   | Calculated for $C_{10}H_{18}N_2O_3Cl_2,\tfrac{1}{4}H_2O$ | Found |
|---|---|---|
| C % | 41.45 | 41.32 |
| H % | 6.39 | 6.33 |
| N % | 9.67 | 9.58 |
| O % | 17.96 | 18.06 |
| Cl % | 24.52 | 24.45 |

EXAMPLE OF PREPARATION NO. 2

Preparation of
4-amino-2-(β-hydroxyethyl)amino-1,3-dimethoxybenzene hydrochloride (compound IC)

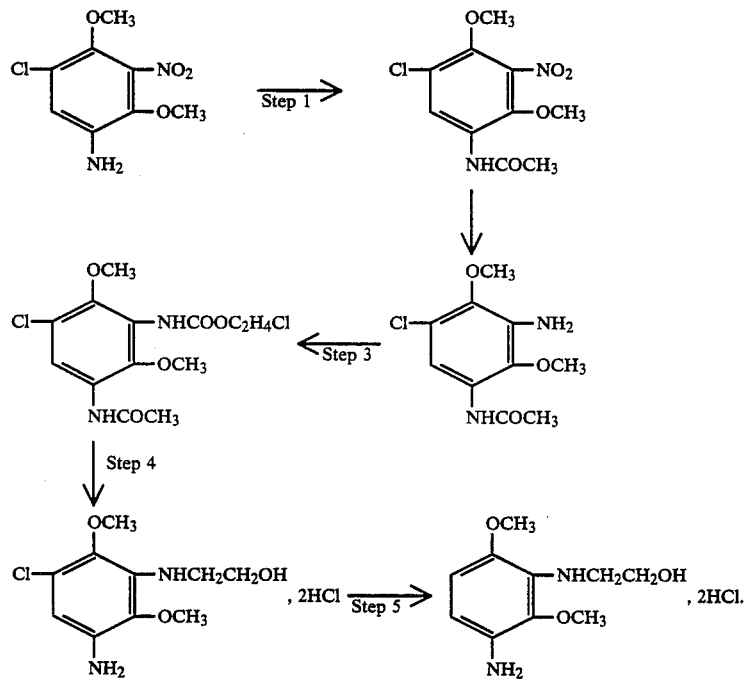

Step 1

Preparation of
5-acetamido-2,4-dimethoxy-3-nitrochlorobenzene 330 ml of acetic anhydride containing a few drops of sulphuric acid were heated to 70° C. 0.7 mole (163 g) of 5-amino-2,4-dimethoxy-3-nitrochlorobenzene prepared according to the operating procedure described in Example 1 (step 1) was added with stirring.

Upon dilution of the reaction mixture with iced water, the expected product precipitated. Recrystallized from 96° strength ethanol, it melted at 115° C.

The elemental analysis of the product obtained was as follows:

|   | Calculated for $C_{10}H_{11}N_2O_5Cl$ | Found |
|---|---|---|
| C % | 43.72 | 43.67 |
| H % | 4.01 | 4.07 |
| N % | 10.20 | 10.17 |
| O % | 29.14 | 29.04 |
| Cl % | 12.93 | 12.98 |

Step 2

Preparation of
5-acetamido-2,4-dimethoxy-3-aminochlorobenzene 253 g of powdered iron which had been reduced with hydrogen were added to 760 ml of water containing 13 ml of acetic acid and which had been previously heated to 80° C., and then 0.46 mole (126.5 g) of 5-acetamido-2,4-dimethoxy-3-nitrochlorobenzene prepared in the previous step was added gradually with stirring. Upon completion of the additions, the reaction mixture was maintained in a boiling water bath for 15 minutes. After cooling, the reaction mixture was centrifuged. The iron slurries, after being separated from the liquid phase, were extracted with ethyl acetate. The ethyl acetate phase which was washed with water and then dried over sodium sulphate was diluted with 100 ml of a 7N hydrochloric acid solution in absolute ethanol. The expected product, which precipitated in the form of hydrochloride was thoroughly drained. It was dissolved in the minimum amount of water. After neutralization, the expected product precipitated. Recrystallized from alcohol, it melted at 113° C.

The elemental analysis of the product obtained was as follows:

| Analysis | Calculated for $C_{10}H_{13}ClN_2O_3$ | Found |
|---|---|---|
| C % | 49.08 | 49.12 |
| H % | 5.32 | 5.31 |
| N % | 11.45 | 11.50 |
| O % | 19.63 | 19.74 |
| Cl % | 14.52 | 14.49 |

Step 3

Preparation of 5-acetamido-2,4-dimethoxy-3-($\beta$-chloroethoxycarbonyl)aminochlorobenzene 0.05 mole (14 g) of 5-acetamido-2,4-dimethoxy-3-aminochlorobenzene hydrochloride obtained according to the previous step, followed by 5.5 ml of 10N sodium hydroxide was added to 70 ml of dioxane. The temperature was raised to the region of 90° C., and then 5 g of calcium carbonate were added. 7.55 g of $\beta$-chloroethyl chloroformate were then introduced with stirring. Upon completion of the addition, heating was maintained for 30 minutes at 90° C. The reaction mixture was diluted with an ice/water mixture after cooling. The expected product precipitated after acidification of the reaction mixture. Recrystallized from ethanol, it melted at 148° C.

The elemental analysis of the product obtained was as follows:

| | Calculated for $C_{13}H_{16}Cl_2N_2O_5$ | Found |
|---|---|---|
| C % | 44.44 | 44.46 |
| H % | 4.56 | 4.54 |
| N % | 7.98 | 7.95 |
| O % | 22.79 | 22.66 |
| Cl % | 20.23 | 20.29 |

Step 4

Preparation of 5-amino-3-($\beta$-hydroxyethyl)amino-2,4-dimethoxychlorobenzene hydrochloride The mixture consisting of 0.25 mole (88 g) of $\beta$-chloroethyl carbamate obtained in the previous step and of 250 ml of 10N sodium hydroxide in 10 ml of water containing 15 ml of ethanol was heated to reflux. After heating for 1 hour, the reaction mixture which was cooled and neutralized was extracted with ethyl acetate. The ethyl acetate phases taken together were evaporated under vacuum after having been washed and dried over sodium sulphate. The solids content obtained was dissolved in isopropyl ether. The expected product precipitated upon addition of a 7N hydrochloric acid solution in absolute ethanol. It was recrystallized from an aqueous-alcoholic mixture containing hydrochloric acid.

The elemental analysis of the product was as follows:

| | Calculated for $C_{10}H_{17}N_2O_3Cl_3$ | Found |
|---|---|---|
| C % | 37.56 | 37.59 |
| H % | 5.32 | 5.36 |
| N % | 8.76 | 8.68 |
| O % | 15.02 | 15.24 |
| Cl % | 33.33 | 33.21 |

Step 5

Preparation of 4-amino-2-($\beta$-hydroxyethyl)amino-1,3-dimethoxybenzene hydrochloride 9.1 g of triethylamine were added to 60 ml of ethanol with 6 ml of water containing 9.3 g of ammonium acetate added thereto, 4.8 g of 10% palladium on charcoal and 0.03 mole (9.6 g) of the compound prepared in the previous step, which had been previously heated to 80° C., followed by slow addition of 3.9 g of formic acid with stirring. Upon completion of the additions, the reaction mixture was maintained for 15 minutes at 80° C. After cooling, the reaction mixture was filtered in order to remove the catalyst. The filtrate which was evaporated to dryness under vacuum was diluted with ethyl acetate. 10 ml of a 7N hydrochloric acid solution in absolute ethanol were added to this solution which had been previously dried over sodium sulphate, in order to precipitate the expected product. The latter was purified by dissolution in a minimum amount of hot water and precipitation via the addition of a 7N solution of hydrochloric acid in absolute ethanol.

The elemental analysis of the product obtained was as follows:

| | Calculated for $C_{10}H_{18}N_2O_3Cl_2$ | Found |
|---|---|---|
| C % | 42.11 | 41.93 |
| H % | 6.32 | 6.38 |
| N % | 9.82 | 9.79 |
| O % | 16.84 | 17.02 |
| Cl % | 24.91 | 24.77 |

EXAMPLE OF PREPARATION NO. 3

Preparation of 2-methylamino-4-amino-1,3-dimethoxybenzene hydrochloride (compound IB)

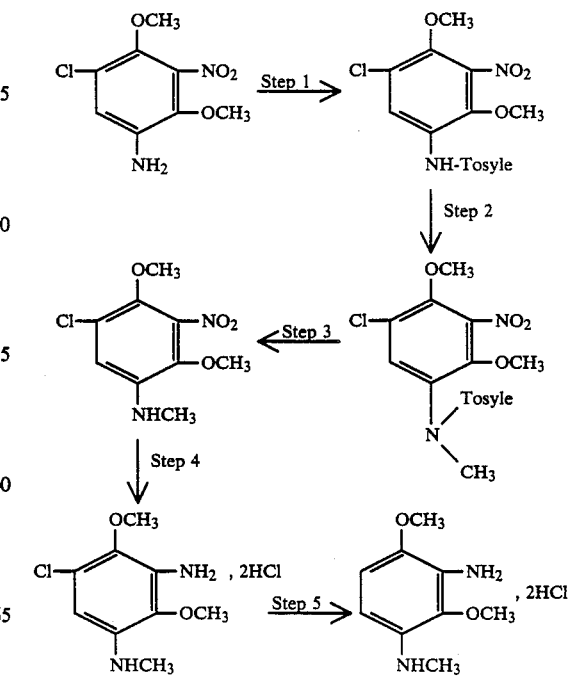

Step 1

Preparation of 5-N-tosylamino-2,4-dimethoxy-3-nitrochlorobenzene

0.11 mole (21 g) of p-toluenesulphonylchloride was added gradually, at 40° C., to a solution of 0.1 mole (23.35 g) of 5-amino-2,4-dimethoxy-3-nitrochlorobenzene prepared in step 1 of Example 1. Stirring was maintained for 15 minutes at 40° C. after completion of the addition.

The reaction mixture was diluted with iced water. Upon acidification using concentrated hydrochloric acid, the expected product precipitated. After thorough draining, washing with water and then with alcohol, the product was dried. It was recrystallized from ethanol.

Elemental analysis of the product obtained gave the following results:

| Analysis | Calculated for $C_{15}H_{15}N_2O_6SCl$ | Found |
|---|---|---|
| C % | 46.57 | 46.49 |
| H % | 3.88 | 3.90 |
| N % | 7.24 | 7.38 |
| O % | 24.84 | 24.56 |
| S % | 8.28 | 8.17 |
| Cl % | 9.18 | 9.35 |

Step 2

Preparation of 5-N,N-tosyl, methylamino-2,4-dimethoxy-3-nitrochlorobenzene

0.022 mole (2.1 ml) of methyl sulphate was added at 30°–35° C. to a solution of 0.02 mole (7.7 g) of 5-N-tosylamino-2,4-dimethoxy-3-nitrochlorobenzene prepared in the previous step in 25 ml of a normal sodium hydroxide solution. Stirring was continued for 15 minutes after completion of the addition. Upon dilution of the reaction mixture with iced water, the expected product precipitated. After thorough draining and washing with water, the product obtained was recrystallized from alcohol.

Analysis of the product obtained gave the following results:

| Analysis | Calculated for $C_{16}H_{17}N_2O_6SCl$ | Found |
|---|---|---|
| C % | 47.94 | 47.96 |
| H % | 4.24 | 4.28 |
| N % | 6.99 | 7.00 |
| O % | 23.97 | 23.94 |
| S % | 7.99 | 7.84 |
| Cl % | 8.86 | 8.91 |

Step 3

Preparation of 5-methylamino-2,4-dimethoxy-3-nitrobenzene

0.025 mole (10 g) of the compound prepared according to the previous step was gradually added to 20 ml of concentrated sulphuric acid, the temperature being maintained at 20° C.; 15 minutes after completion of the addition, the reaction mixture was diluted with an ice-/water mixture. The expected product which precipitated, was thoroughly drained, washed with water, and dried under vacuum in the presence of $P_2O_5$. It was recrystallized from cyclohexane; it melted at 57° C.

Analysis of the product obtained gave the following results:

| Analysis | Calculated for $C_9H_{11}N_2O_4Cl$ | Found |
|---|---|---|
| C % | 43.81 | 43.77 |
| H % | 4.46 | 4.55 |
| N % | 11.36 | 11.35 |
| O % | 25.96 | 26.12 |
| Cl % | 14.40 | 14.36 |

Step 4

Preparation of 5-methylamino-3-amino-2,4-dimethoxychlorobenzene hydrochloride

50 g of powdered iron which had been reduced with hydrogen were added to 200 ml of water containing 2.5 ml of acetic acid and previously heated in a boiling water bath and then, 0.1 mole (24.65 g) of 5-methylamino-2,4-dimethoxy-3-nitrochlorobenzene obtained according to the operating procedure of step 3 was added gradually with stirring. Upon completion of the additions, heating was maintained for an additional 15 minutes. The reaction mixture was centrifuged, the expected product was extracted from the iron slurries with ethyl acetate. The ethylacetate phases were washed with water, and then dried over anhydrous sodium sulphate. Upon addition of 43 ml of a 7N hydrochloric acid solution in ethanol, the expected product was precipitated. After thorough draining of the precipitate, washing with ethanol and then drying, the product obtained was recrystallized from an aqueous-alcoholic solution of hydrochloric acid.

Analysis of the product obtained gave the following results:

| Analysis | Calculated for $C_9H_{15}N_2O_2Cl_3$ | Found |
|---|---|---|
| C % | 37.31 | 37.21 |
| H % | 5.18 | 5.23 |
| N % | 9.67 | 9.54 |
| O % | 11.05 | 11.10 |
| Cl % | 36.79 | 36.86 |

Step 5

Preparation of 4-methylamino-2-amino-1,3-dimethoxybenzene hydrochloride

The mixture consisting of 8.5 g of ammonium acetate, 7.5 g of 10% palladium on charcoal, 0.05 mole (15 g) of 5-methylamino-3-amino-2,4-dimethoxychlorobenzene hydrochloride in 14 ml of water containing 90 ml of ethanol and 15.2 g of triethylenediamine, was heated to 70° C. with stirring, and then 6.44 g of formic acid were added dropwise. Heating was maintained for 1 hour after completion of the addition. The catalyst was removed by filtration. The solids content obtained by evaporation of the filtrate under vacuum was dissolved in ethyl acetate. A 7N hydrochloric acid solution in absolute ethanol was added to the ethyl acetate which had been dried over sodium sulphate, in order to precipitate the expected product. The latter was recrystallized while hot from an aqueous-alcoholic solution of hydrochloric acid.

The analysis of the product obtained was as follows:

| Analysis | Calculated for $C_9H_{16}N_2O_2Cl_2$ | Found |
|---|---|---|
| C % | 42.35 | 42.36 |
| H % | 6.27 | 6.35 |
| N % | 10.98 | 10.88 |
| O % | 12.55 | 12.70 |
| Cl % | 27.84 | 27.81 |

EXAMPLE OF PREPARATION NO. 4

Preparation of 2,4-bis(β-hydroxyethyl)amino-1,3-dimethoxybenzene hydrochloride

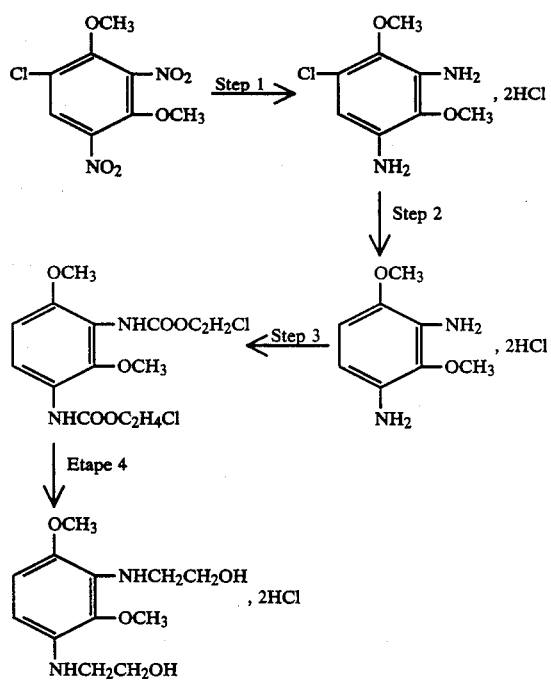

Step 1

Preparation of 2,4-dimethoxy-3,5-diaminochlorobenzene hydrochloride 100 g of powdered iron which had been reduced with hydrogen were added to 270 ml of water containing 27 ml of acetic acid which had been previously heated to 80° C., and then 0.25 mole (66 g) of 2,4-dimethoxy-3,5-dinitrochlorobenzene was added gradually, with stirring. Upon completion of the additions, the reaction mixture was maintained in a boiling water bath for 30 additional minutes. After cooling, the reaction mixture was centrifuged. The iron slurries which contained the expected product were taken up with acetone under vigorous mixing. Upon filtration of the iron slurries followed by washing with acetone, the expected product precipitated from the acetone filtrate upon addition of a hydrochloric acid solution in ethanol. After thorough draining and washing, the expected product was recrystallized while hot from a hydrochloric acid and water mixture.

Elemental analysis of the product obtained gave the following results:

| Analysis | Calculated for $C_8H_{13}N_2Cl_3O_2$ | Found |
|---|---|---|
| C % | 34.85 | 34.85 |
| H % | 4.72 | 4.82 |
| N % | 10.16 | 10.03 |
| O % | 11.62 | 11.80 |
| Cl % | 38.66 | 38.46 |

Step 2

Preparation of 2,4-diamino-1,3-dimethoxybenzene hydrochloride

The mixture consisting of 77 g of ammonium acetate, 42 g of 10% palladium on charcoal, 0.25 mole (69 g) of 2,4-dimethoxy-3,5-diaminochlorobenzene hydrochloride in 420 ml of ethanol containing 50 ml of water was heated to 75° C. with stirring. 75 g of triethylamine were added and then, 31 g of formic acid were added dropwise. After 30 minutes of additional heating, the reaction mixture was filtered while hot. The filtrate was evaporated to dryness. Upon addition of ethyl acetate, the inorganic salts were precipitated and removed by thorough draining. 10 ml of an alcoholic solution of 7N hydrochloric acid were added to the filtrate which had been dried over sodium sulphate. The expected product precipitated, it was recrystallized from a mixture of water and a solution of hydrochloric acid in ethanol.

Elemental analysis of the product obtained gave the following results:

| Analysis | Calculated for $C_8H_{14}N_2O_2Cl_2$ | Found |
|---|---|---|
| C % | 39.83 | 39.75 |
| H % | 5.81 | 5.79 |
| N % | 11.62 | 11.60 |
| O % | 13.28 | 13.54 |
| Cl % | 29.46 | 29.29 |

Step 3

Preparation of 2,4-bis(β-chloroethoxycarbonyl)amino-1,3-dimethoxy benzene 0.05 mole (12.05 g) of 2,4-diamino-1,3-dimethoxybenzene hydrochloride was added to 90 ml of dioxane, followed by 10 ml of 10N sodium hydroxide. The temperature was raised to the region of 85°–90° C. and then 10 g of calcium carbonate were added. 15 g of β-chloroethyl chloroformate were then introduced with stirring. Upon completion of the addition, heating was maintained at 90° C. for 15 minutes. The reaction mixture was diluted with 500 g of iced water. Upon acidification of the reaction mixture, the expected product slowly precipitated. After thorough draining, washing with water and drying under vacuum in the presence of $P_2O_5$, it could be recrystallized from benzene. It melted at 105° C.

Analysis of the product obtained gave the following results:

| Analysis | Calculated for $C_{14}H_{18}N_2O_6Cl_2$ | Found |
|---|---|---|
| C % | 44.09 | 43.99 |
| H % | 4.72 | 4.77 |
| N % | 7.35 | 7.31 |
| O % | 25.20 | 25.25 |
| Cl % | 18.60 | 18.72 |

Step 4

Preparation of 2,4-bis(β-hydroxyethyl)amino-1,3-dimethoxybenzene hydrochloride The mixture consisting of 0.22 mole (83 g) of 2,4-bis(β-chloroethoxycarbonyl)amino-1,3-dimethoxybenzene prepared according to the operating procedure described in step 3 and 200 ml of 10N sodium hydroxide in 200 ml of alcohol containing 100 ml of water was heated for 1 hour under reflux.

The alcohol was driven off under reduced pressure. Upon neutralization of the water, the product was extracted with ethyl acetate. The expected product was obtained by addition of a hydrochloric acid solution in absolute ethanol to the ethyl acetate phases which had been previously dried over sodium sulphate. After thorough draining, followed by drying under vacuum in the presence of $P_2O_5$, the product was recrystallized from an aqueous-alcoholic solution of hydrochoric acid.

Analysis of the product obtained gave the following results:

| Analysis | Calculated for $C_{12}H_{22}N_2O_4Cl_2$ | Found |
|---|---|---|
| C % | 43.77 | 43.39 |
| H % | 6.69 | 6.76 |
| N % | 8.51 | 8.44 |
| O % | 19.45 | 19.92 |
| Cl % | 21.58 | 21.39 |

EXAMPLE OF PREPARATION NO. 5 (PROCESS I)

Preparation of 2,4-diamino-1,3-diethoxybenzene hydrochloride

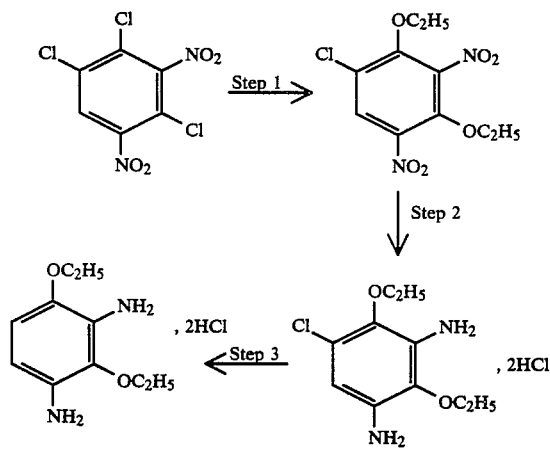

Step 1

Preparation of 3,5-dinitro-2,4-diethoxychlorobenzene 0.1 mole (27.15 g) of 3,5-dinitro-1,2,4-trichlorobenzene was heated to 75° C. in 110 ml of absolute ethanol. 0.2 mole of a 15% solution of sodium ethylate in absolute ethanol was added. Upon completion of the addition, the reaction mixture was heated for 30 minutes at 75° C., and then diluted with 300 g of an ice/water mixture. The expected product precipitated. After drying under vacuum and recrystallization from isopropyl ether, it melted at 78° C.

The elemental analysis of the product obtained was as follows:

| Analysis | Calculated for $C_{20}H_{11}N_2O_6Cl$ | Found |
|---|---|---|
| C % | 41.31 | 41.22 |
| H % | 3.79 | 3.81 |
| N % | 9.64 | 9.65 |
| O % | 33.05 | 32.88 |
| Cl % | 12.22 | 12.07 |

Step 2

Preparation of 2,4-diethoxy-3,5-diaminochlorobenzene hydrochloride 170 g of powdered iron which had been reduced with hydrogen were added to 450 ml of water containing 8.5 ml of acetic acid which have previously been heated to 80° C., and then 0.3 mole (87 g) of 3,5-dinitro-2,4-diethoxychlorobenzene was then gradually added with stirring. Upon completion of the additions, the reaction mixture was maintained in a boiling water bath for 30 additional minutes. After cooling, the reaction mixture was centrifuged. The iron slurries were made to a paste again with ethyl acetate and the mother liquors were extracted with ethyl acetate. The ethyl acetate phases, joined together, were washed with water and then dried over $Na_2SO_4$. Upon addition of a hydrochloric acid solution in ethanol, the expected product precipitated. After thorough draining, it was washed with acetone. It was recrystallized from an aqueous-alcoholic solution of hydrochloric acid.

Analysis of the product obtained gave the following results:

| Analysis | Calculated for $C_{10}H_{17}N_2O_2Cl_3$ | Found |
|---|---|---|
| C % | 39.54 | 39.67 |
| H % | 5.60 | 5.64 |
| N % | 9.23 | 9.26 |
| O % | 10.54 | 10.48 |
| Cl % | 35.09 | 35.26 |

Step 3

Preparation of 2,4-diamino-1,3-diethoxybenzene hydrochloride

The mixture consisting of 7.7 g of ammonium acetate, 3.8 g of 10% palladium on charcoal, 0.025 mole (7.6 g) of 2,4-diethoxy-3,5-diaminochlorobenzene hydrochloride in 42 ml of ethanol containing 5 ml of water was heated to 70° C. with stirring. 7.5 g of triethylamine were added and then, 3.1 g of formic acid were added dropwise. After 20 additional minutes of heating at 80° C., the reaction mixture was filtered while hot. The filtrate was evaporated to dryness. Upon addition of ethyl acetate, the inorganic salts were precipitated and removed by filtration. 10 ml of a 7N alcoholic solution of hydrochloric acid were added to the filtrate which was dried over sodium sulphate. The expected product precipitated; it was recrystallized from a 6N hydrochloric acid solution.

Analysis of the product obtained gave the following results:

| Analysis | Calculated for $C_{10}H_{18}N_2O_2Cl_2$ | Found |
|---|---|---|
| C % | 44.61 | 44.70 |

-continued

| Analysis | Calculated for $C_{10}H_{18}N_2O_2Cl_2$ | Found |
|---|---|---|
| H % | 6.69 | 6.75 |
| N % | 10.41 | 10.37 |
| O % | 11.90 | 12.00 |
| Cl % | 26.39 | 26.29 |

EXAMPLE OF PREPARATION NO. 6 (PROCESS II)

Preparation of 2,4-diamino-1,3-diethoxybenzene hydrochloride (directly from 2,4-diethoxy-3,5-dinitrochlorobenzene)

The mixture consisting of 0.1 mole (29 g) of 2,4-diethoxy-3,5-dinitrochlorobenzene, 15.4 g of ammonium acetate and 5.2 g of 10% palladium on charcoal in 100 ml of ethanol containing 15 ml of water was heated to 80° C. for 1 hour under a pressure of 20 kg of hydrogen.

The reaction mixture was filtered while hot in order to remove the catalyst. The filtrate was evaporated to dryness under reduced pressure. Ethyl acetate was added in order to precipitate the inorganic salts which were removed by thorough draining. Upon drying over sodium sulphate, the expected product was precipitated by addition of a 7N hydrochloric acid solution in absolute ethanol. The product obtained in this way was identical to the product prepared in Example of preparation No. 5.

EXAMPLE OF PREPARATION NO. 7

Preparation of 2,4-diamino-1,3-bis-(γ-hydroxypropoxy)benzene hydrochloride

Step 1

Preparation of 3,5-dinitro-2,4-bis-(γ-hydroxypropoxy)chlorobenzene 1 mole (271.5 g) of 3,5-dinitro-1,2,4-trichlorobenzene in 700 ml of 1,3-propanediol was heated to 85° C. 2 moles of powdered potassium hydroxide dissolved in 280 ml of 1,3-propanediol were added over 30 minutes. The reaction mixture was heated for 1 hour at 85° C. upon completion of the additions. After cooling, the expected product was filtered off, washed with water and then dissolved in 1.5 liters of ethyl acetate which, after washing with water, was dried over sodium sulphate. Upon concentration to dryness, a precipitate was obtained which, after having recrystallized from isopropyl ether, melted at 90° C.

Analysis of the product obtained gave the following results:

| Analysis | Calculated for $C_{12}H_{15}N_2O_8Cl$ | Found |
|---|---|---|
| C % | 41.08 | 41.12 |
| H % | 4.28 | 4.33 |
| N % | 7.99 | 8.04 |
| O % | 36.52 | 36.45 |
| Cl % | 10.13 | 10.09 |

Step 2

Preparation of 2,4-bis-(γ-hydroxypropoxy)-3,5-diaminochlorobenzene hydrochloride 250 g of powdered iron which had been reduced with hydrogen were added to 700 ml of water containing 10 ml of acetic acid which had been previously heated to 95° C., and 0.34 mole (119 g) of 3,5-bisnitro-2,4-bis-(γ-hydroxypropoxy)chlorobenzene was added gradually with stirring. Upon completion of the additions, the reaction mixture was maintained for 10 additional minutes at 95° C. After cooling, 1 liter of ethyl acetate was added. The reaction mixture was filtered off in order to remove the iron slurries. The ethyl acetate phase which was separated from the aqueous phase, was, after washing with water and drying over sodium sulphate evaporated off to dryness. The solids content obtained in this manner was taken up with a hydrochloric acid solution in absolute ethanol. The expected product precipitated. After thorough draining followed by drying, analysis of the product obtained gave the following results:

| Analysis | Calculated for $C_{12}H_{21}N_2O_4Cl_3$ | Found |
|---|---|---|
| C % | 39.62 | 39.49 |
| H % | 5.87 | 5.67 |
| N % | 7.70 | 7.56 |
| O % | 17.61 | 17.81 |
| Cl % | 29.30 | 29.26 |

Step 3

Preparation of 2,4-diamino-1,3-bis-(γ-hydroxypropoxy)benzene hydrochloride 0.45 mole (63.6 ml) of triethylamine was added to the mixture consisting of 47 g of ammonium acetate, 26 g of palladium on charcoal and 0.15 mole (55 g) of 2,4-bis-(γ-hydroxypropyl)-3,5-diaminochlorobenzene hydrochloride in 270 ml of ethanol containing 27 ml of water. 0.4 mole (18.4 g) of formic acid was added gradually (strong exothermic character) over approximately 15 minutes was added to the latter reaction mixture which was heated to reflux. The reaction mixture was filtered off while hot in order to remove the catalyst and then concentrated to dryness. Upon addition of ethyl acetate, the inorganic salts precipitated; after filtering them off, a 7N alcoholic solution of hydrochloric acid was added: the expected product crystallized.

Analysis of the product obtained gave the following results:

| Analysis | Calculated for $C_{12}H_{22}N_2O_4Cl_2$ | Found |
|---|---|---|
| C % | 43.77 | 43.82 |
| H % | 6.69 | 6.67 |
| N % | 8.51 | 8.40 |
| O % | 19.45 | 19.68 |
| Cl % | 21.58 | 21.48 |

DYEING EXAMPLE 1

The following dyeing mixture is prepared:

| | |
|---|---|
| 4-(β-Hydroxyethyl)amino-2-amino-1,3-dimethoxybenzene dihydrochloride | 0.71 g |
| p-Phenylenediamine | 0.25 g |
| CEMULSOL NP 4 - RHONE POULENC (nonylphenol oxyethylenated with 4 moles EO) | 12 g |
| CEMULSOL NP 9 - RHONE POULENC (nonylphenol oxyethylenated with 9 moles EO) | 15 g |
| Oleyl alcohol polyglycerolated with 2 moles of glycerol | 1.5 g |
| Oleyl alcohol polyglycerolated with 4 moles of glycerol | 1.5 g |
| Propylene glycol | 6 g |

-continued

| | |
|---|---|
| TRILON G (ethylenediaminetetraacetic acid) | 0.12 g |
| Ammonia solution, 22° Be | 11 g |
| Thioglycolic acid | 0.6 g |
| Water qs | 100 g |
| pH: 10.4 | |

At the time of use, 100 g of "20 volumes" hydrogen peroxide are added. When applied for 25 minutes at 35° C. on hair which is naturally 90% white, the mixture imparts to the latter, after shampooing and rinsing, a dark grey-purple colouration.

DYEING EXAMPLE 2

The following dyeing mixture is prepared:

| | |
|---|---|
| 4-(β-Hydroxyethyl)amino-2-amino-1,3-dimethoxybenzene dihydrochloride | 0.71 g |
| p-Tolylenediamine dihydrochloride | 0.49 g |
| ALFOL C 16/18 - company CONDEA (cetyl/stearyl alcohol) | 19 g |
| EUTANOL G - company HENKEL (2-octyldodecanol) | 4.5 g |
| MERGITAL C.S. - company HENKEL (cetyl/stearyl alcohol with 15 moles EO) | 2.5 g |
| Ammonium lauryl sulphate | 10 g |
| Cationic polymer containing the following repeated unit: | 4 g |

$$\left[ \begin{array}{cc} CH_3 & CH_3 \\ | & | \\ -N^\oplus-(CH_2)_3-N^\oplus-(CH_2)_6- \\ | & | \\ CH_3 \ Cl^\ominus & CH_3 \ Cl^\ominus \end{array} \right]$$

| | |
|---|---|
| of MW about 10,000 | |
| Benzyl alcohol | 2 g |
| Ammonia solution, 22° Be | 11 ml |
| TRILON B (ethylenediaminetetracetic acid) | 1 g |
| Sodium bisulphite 35° Be | 1.2 g |
| Water qs | 100 g |
| pH: 9.2 | |

At the time of use, 100 g of "20 volumes" hydrogen peroxide are added. When applied for 25 minutes at 35° C. on bleached hair, the mixture imparts to the latter, after shampooing and rinsing, a dark violet colouration.

DYEING EXAMPLE 3

The following dyeing mixture is prepared:

| | |
|---|---|
| 4-Amino-2-(β-hydroxyethyl)amino-1,3-dimethoxybenzene dihydrochloride | 0.71 g |
| p-Phenylenediamine | 0.27 g |
| Oleyl alcohol polyglycerolated with 2 moles of glycerol | 4.5 g |
| Oleyl alcohol polyglycerolated with 4 moles of glycerol | 4.5 g |
| ETHOMEE 0 12 - company ARMOON HESS CHEMICAL Ltd (oleylamine oxyethylenated with 12 moles of EO) | 4.5 g |
| COMPERLAN KD - company HENKEL (coconut diethanolamide) | 9 g |
| Propylene glycol | 4 g |
| 2-Butoxyethanol | 8 g |
| Ethanol, 96° strength | 6 g |
| MASQUOL DTPA - company PROTEX (pentasodium salt of diethylenetriaminepentaacetic acid) | 2 g |
| Hydroquinone | 0.15 g |
| Sodium bisulphite solution, 35° Be | 1.3 g |
| Ammonia solution, 22° Be | 10 g |
| Water qs | 100 g |
| pH: 10 | |

At the time of use, 100 g of "20 volumes" hydrogen peroxide are added. When applied for 20 minutes at 35° C. on hair which is naturally 90% white, the mixture imparts to the latter, after shampooing and rinsing, a greyish purple-blue colouration.

DYEING EXAMPLE 4

The following dyeing mixture is prepared:

| | |
|---|---|
| 4-Methylamino-2-amino-1,3-dimethoxybenzene dihydrochloride | 0.64 g |
| p-Phenylenediamine | 0.27 g |
| ALFOL C 16/18 - company CONDEA (cetyl/steryl alcohol) | 19 g |
| EUTANOL G - company HENKEL (2-octyldodecanol) | 4.5 g |
| MERGITAL C.S. - company HENKEL (cetyl/stearyl alcohol with 15 moles EO) | 2.5 g |
| Ammonium Lauryl sulphate | 10 g |
| Cationic polymer containing the following repeated unit: | 4 g |

$$\left[ \begin{array}{cc} CH_3 & CH_3 \\ | & | \\ -N^\oplus-(CH_2)_3-N^\oplus-(CH_2)_6- \\ | & | \\ CH_3 \ Cl^\ominus & CH_3 \ Cl^\ominus \end{array} \right]$$

| | |
|---|---|
| of MW about 10,000 | |
| Benzyl alcohol | 2 g |
| Ammonia solution, 22° Be | 11 g |
| TRILON B (ethylenediaminetetraacetic acid) | 1 g |
| Sodium bisulphite, 35° Be | 1.2 g |
| Water qs | 100 g |
| pH: 9.3 | |

At the time of use, 100 g of "20 volumes" hydrogen peroxide are added. When applied for 20 minutes at 35° C. on hair which is naturally 90% white, the mixture imparts to the latter, after shampooing and rinsing, a dark red-purple colouration.

DYEING EXAMPLE 5

The following dyeing mixture is prepared:

| | |
|---|---|
| 2,4-Bis(β-hydroxyethyl)amino-1,3-dimethoxybenzene dihydrochloride | 0.82 g |
| p-Phenylenediamine | 0.27 g |
| CARBOPOL 934 - company GOODRICH CHEMICALS | 3 g |
| Alcohol, 96° strength | 11 g |
| 2-Butoxyethanol | 5 g |
| Trimethylcetylammonium bromide | 2 g |
| TRILON B (ethylenediaminetetracetic acid) | 0.2 g |
| Ammonia solution, 22° Be | 10 g |
| Sodium bisulphite, 35° Be | 1 g |
| Water qs | 100 g |
| pH: 9.5 | |

At the time of use, 100 g of "20 volumes" hydrogen peroxide are added. When applied for 20 minutes at 35° C. on hair which is naturally 90% white, the mixture imparts to the latter, after shampooing and rinsing, a slightly grey dark purple colouration.

DYEING EXAMPLE 6

The following dyeing mixture is prepared.

| | |
|---|---|
| 4-Amino-2-(β-hydroxyethyl)amino-1,3-dimethoxybenzene dihydrochloride | 0.71 g |
| p-Aminophenol | 0.27 g |
| Oleyl alcohol polyglycerolated with 2 moles of glycerol | 4.5 g |
| Oleyl alcohol polyglycerolated with 4 moles of glycerol | 4.5 g |
| ETHOMENN 0 12 - company ARMOON HESS CHEMICAL Ltd (oleylamine oxyethylenated with 12 moles of EO) | 4.5 g |
| COMPERLAN KD - company HENKEL (coconut diethanolamide) | 4 g |
| Propylene glycol | 4 g |
| 2-Butoxyethanol | 8 g |
| Ethanol, 96° strength | 6 g |
| MASQUOL DTPA - company PROTEX (pentasodium salt of diethylenetriaminepentaacetic acid) | 2 g |
| Hydroquinone | 0.15 g |
| Sodium bisulphite solution, 35° Be | 1.3 g |
| Ammonia solution, 22° Be | 10 g |
| Water qs | 100 g |
| pH: 9.9 | |

At the time of use, 100 g of "20 volumes" hydrogen peroxide was added. When applied for 20 minutes at 35° C. on bleached hair, the mixture imparts to the latter, after shampooing and rinsing, a greyish red colouration.

DYEING EXAMPLE 7

The following dyeing mixture is prepared:

| | |
|---|---|
| 4-(β-Hydroxyethyl)amino-2-amino-1,3-dimethoxybenzene dihydrochloride | 0.71 g |
| p-Aminophenol | 0.27 g |
| Oleyl alcohol polyglycerolated with 2 moles of glycerol | 4.5 g |
| Oleyl alcohol polyglycerolated with 4 moles of glycerol | 4.5 g |
| ETHOMEEN 0 12 - company ARMOON HESS CHEMICAL Ltd (oleylamine oxyethylenated with 12 moles of EO) | 4.5 g |
| COMPERLAN KD - company HENKEL (coconut diethanolamide) | 9 g |
| Propylene glycol | 4 g |
| 2-Butoxyethanol | 8 g |
| Ethanol, 96° strength | 6 g |
| MASQUOL DTPA - company PROTEX (pentasodium salt of diethylenetriaminepentaacetic acid) | 2 g |
| Hydroquinone | 0.15 g |
| Sodium bisulphite solution, 35° Be | 1.3 g |
| Ammonia solution, 22° Be | 10 g |
| Water qs | 100 g |
| pH: 9.9 | |

At the time of use, 100 g of "20 volumes" hydrogen peroxide are added. When applied for 20 minutes at 35° C. on hair which is naturally 90% white, the mixture imparts to the latter, after shampooing and rinsing, a slightly grey light red-brown colouration.

DYEING EXAMPLE 8

| | |
|---|---|
| 4-(β-Hydroxyethyl)amino-2-amino-1,3-dimethoxybenzene dihydrochloride | 0.12 g |
| p-Phenylenediamine | 0.08 g |
| p-Aminophenol | 0.16 g |
| meta-Aminophenol | 0.13 g |
| Resorcinol | 0.13 g |
| 2-Methyl-5-[N-(β-hydroxyethyl)amino]phenol | 0.1 g |
| CARBOPOL 934 - company GOODRICH CHEMICALS | 3 g |
| Alcohol, 96° strength | 11 g |
| 2-Butoxyethanol | 5 g |
| Trimethylcetylammonium bromide | 2 g |
| TRILON B (ethylenediaminetetraacetic acid) | 0.2 g |
| Ammonia solution, 22° Be | 10 g |
| Sodium bisulphite, 35° Be | 1 g |
| Water qs | 100 g |
| pH: 9.5 | |

At the time of use, 100 g of "20 volumes" hydrogen peroxide are added. When applied for 20 minutes at 35° C. on hair which is naturally 90% white, the mixture imparts to the latter, after shampooing and rinsing, a slightly grey red-brown colouration.

DYEING EXAMPLE 9

The following dyeing mixture is prepared:

| | |
|---|---|
| 4-Methylamino-2-amino-1,3-dimethoxybenzene dihydrochloride | 0.64 g |
| Isopropyl-p-phenylenediamine dihydrochloride | 0.56 g |
| CARBOPOL 934 - company GOODRICH CHEMICALS | 3 g |
| Alcohol, 96° strength | 11 g |
| 2-Butoxyethanol | 5 g |
| Trimethylcetylammonium bromide | 2 g |
| TRILON B (ethylenediaminetetraacetic acid) | 0.2 g |
| Sodium bisulphite, 35° Be | 1 g |
| Ammonia solution, 22° Be | 10 g |
| Water qs | 100 g |
| pH: 9.3 | |

At the time of use, 100 g of "20 volumes" hydrogen peroxide are added. When applied for 25 minutes at 35° C. on hair which is naturally 90% white, the mixture imparts to the latter, after shampooing and rinsing, a bilberry-red colouration.

DYEING EXAMPLE 10

The following dyeing mixture is prepared:

| | |
|---|---|
| 4-Amino-2-(β-hydroxyethyl)amino-1,3-dimethoxybenzene dihydrochloride | 1.42 g |
| 1,4-Diamino-2,6-dimethylbenzene | 1.05 g |
| ALFOL 16/18 - company CONDEA (cetyl/stearyl alcohol) | 8 g |
| CIRE DE LANETTE E - company HENKEL (sodium cetyl/stearyl sulphate) | 0.5 g |
| CEMULSOL B - RHONE POULENC (ethoxylated castor oil) | 1 g |
| Oleic diethanolamide | 1.5 g |
| MASQUOL DTPA - company PROTEX (pentasodium salt of diethylenetriaminepentaacetic acid) | 2.5 g |
| Ammonia solution, 22° Be | 11 g |
| Sodium bisulphite solution, 35° Be | 1 g |
| Water qs | 100 g |
| pH: 10 | |

At the time of use, 100 g of "20 volumes" hydrogen peroxide are added. When applied for 25 minutes at 35° C. on hair which is naturally 90% white, the mixture imparts to the latter, after shampooing and rinsing, a navy blue colouration.

DYEING EXAMPLE 11

The following dyeing mixture is prepared:

| | |
|---|---|
| 2,4-Diamino-1,3-bis(γ-hydroxypropoxy)benzene dihydrochloride | 1 g |
| 4-Amino-N-(β-methoxyethyl)aniline dihydrochloride | 0.71 g |

-continued

| | |
|---|---|
| CEMULSOL NP 4 - RHONE POULENC (nonylphenol oxyethylenated with 4 moles EO) | 12 g |
| CEMULSOL NP 9 - RHONE POULENC (nonylphenol oxyethylenated with 9 moles EO) | 15 g |
| Oleyl alcohol polyglycerolated with 2 moles of glycerol | 1.5 g |
| Oleyl alcohol polyglycerolated with 4 moles of glycerol | 1.5 g |
| Propylene glycol | 6 g |
| TRILON B (ethylenediaminetetraacetic acid) | 0.12 g |
| Ammonia solution, 22° Be | 11 g |
| Water qs | 100 g |
| pH: 10 | |

At the time of use, 90 g of "20 volumes" hydrogen peroxide are added. When applied for 25 minutes at 35° C. on hair which is naturally 90% white, the mixture imparts to the latter, after shampooing and rinsing, a Thames blue colouration.

DYEING EXAMPLE 12

The following dyeing mixture is prepared:

| | |
|---|---|
| 2,4-Diamino-1,3-diethoxybenzene dihydrochloride | 0.75 g |
| N,N-Bis($\beta$-hydroxyethyl)-para-phenylenediamine dihydrochloride | 0.75 g |
| ALFOL C 16/18 - company CONDEA (cetyl/stearyl alcohol) | 8 g |
| CIRE DE LANETTE E - company HENKEL (sodium cetyl/stearyl sulphate) | 0.5 g |
| CEMULSOL B - RHONE POULENC (ethoxylated castor oil) | 1 g |
| Oleic diethanolamide | 1.5 g |
| MASQUOL DTPA - company PROTEX (pentasodium salt of diethylenetriaminepentaacetic acid) | 2.5 g |
| Ammonia solution, 22° Be | 11 g |
| Water qs | 100 g |
| pH: 10.2 | |

At the time of use, 100 g of "20 volumes" hydrogen peroxide are added. When applied for 10 minutes at 35° C. on bleached hair, the mixture imparts to the latter, after shampooing and rinsing, a dark blue colouration.

We claim:

1. A hair dye composition comprising in a cosmetically acceptable aqueous vehicle, 0.05 to 3.5 weight percent of at least one compound, as a coupler, having the formula

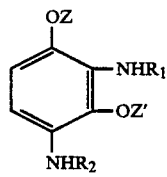

(I)

wherein
R$_1$ and R$_2$, each independently, represent hydrogen, alkyl having 1-4 carbon atoms, monohydroxyalkyl having 2-3 carbon atoms or polyhydroxyalkyl having 2-3 carbon atoms,
Z and Z', each independently, represent alkyl having 1-4 carbon atoms or hydroxyalkyl having 2-4 carbon atoms, with the proviso that, when R$_1$ and R$_2$ simultaneously represent hydrogen, Z and Z' do not simultaneously represent methyl, and the acid addition salt thereof, in combination with at least one oxidation dye precursor of the para type in an amount effective to dye said hair.

2. The hair dye composition of claim 1 wherein said oxidation dye precursor of the para type is selected from the group consisting of a para-phenylenediamine, a para-aminophenol, a heterocyclic para compound and a mixture thereof.

3. The hair dye composition of claim 2 wherein said para-phenylenediamine has the formula

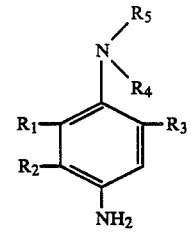

(XII)

wherein
R$_1$, R$_2$ and R$_3$, each independently represent hydrogen, halogen, alkyl having 1-4 carbon atoms or alkoxy having 1-4 carbon atoms,
R$_4$ and R$_5$, each independently, represent hydrogen, alkyl having 1-4 carbon atoms, hydroxyalkyl having 1-4 carbon atoms, alkoxyalkyl wherein the alkoxy moiety has 1-4 carbon atoms and the alkyl moiety has 1-4 carbon atoms, carbamylalkyl wherein the alkyl moiety has 1-4 carbon atoms, mesylaminoalkyl wherein the alkyl moiety has 1-4 carbon atoms, acetylaminoalkyl wherein the alkyl moiety has 1-4 carbon atoms, ureidoalkyl wherein the alkyl moiety has 1-4 carbon atoms, carbethoxyaminoalkyl wherein the alkyl moiety has 1-4 carbon atoms, piperidinoalkyl wherein the alkyl moiety has 1-4 carbon atoms or morpholinoalkyl wherein the alkyl moiety has 1-4 carbon atoms, or
R$_4$ and R$_5$, together with the nitrogen atom to which they are attached, form a piperidino or morpholino heterocycle,
with the proviso that R$_1$ and R$_3$ represent hydrogen when R$_4$ and R$_5$ are other than hydrogen, or
the salt of said compound of formula (XII).

4. The hair dye composition of claim 3 wherein said para-phenylenediamine is selected from the group consisting of
p-phenylenediamine,
p-tolylenediamine,
methoxy-para-phenylenediamine,
chloro-para-phenylenediamine,
2,6-dimethyl-p-phenylenediamine,
2,5-dimethyl-p-phenylenediamine,
2-methyl-5-methoxy-p-phenylenediamine,
2,6-dimethyl-5-methoxy-p-phenylenediamine,
N,N-dimethyl-p-phenylenediamine,
3-methyl-4-amino-N,N-diethylaniline,
N,N-bis ($\beta$-hydroxyethyl)-p-phenylenediamine,
3-methyl-4-amino-N,N-bis ($\beta$-hydroxyethyl) aniline,
3-chloro-4-amino-N,N-bis ($\beta$-hydroxyethyl) aniline,
4-amino-N-ethyl-N-(carbamylmethyl) aniline,
3-methyl-4-amino-N-ethyl-N-(carbamylmethyl) aniline,
4-amino-N-ethyl-N-($\beta$-piperidinoethyl) aniline,
3-methyl-4-amino-N-ethyl-N-($\beta$-piperidinoethyl) aniline,
4-amino-N-ethyl-N-($\beta$-morpholinoethyl) aniline, 3-methyl-4-amino-N-ethyl-N-(βmorpholinoethyl) aniline,
4-amino-N-ethyl-N-(β-acetylaminoethyl) aniline,
4-amino-N-(β-methoxyethyl) aniline,
3-methyl-4-amino-N-ethyl-N-(β-acetylaminoethyl) aniline,
4-amino-N-ethyl-N-(β-mesylaminoethyl) aniline,
3-methyl-4-amino-N-ethyl-N-(βmesylaminoethyl) aniline,
4-amino-N-ethyl-N-(β-sulphoethyl) aniline,
3-methyl-4-amino-N-ethyl-N-(β-sulphoethyl) aniline,
N-(4-aminophenyl) morpholine,
N-(4-aminophenyl) piperidine,
2,3-dimethyl-p-phenylenediamine and
isopropyl-p-phenylenediamine,
said para-phenylenediamine being in free base or cosmetically acceptable salt form.

5. The hair dye composition of claim 2 wherein said para-aminophenol is selected from the group consisting of p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl)-4-aminophenol, 2-methoxy-4-aminophenol and 3-methoxy-4-aminophenol.

6. The hair dye composition of claim 2 wherein said heterocyclic para compound is selected from the group consisting of 2,5-diaminopyridine, 2-hydroxy-5-aminopyridine and tetraaminopyrimidine.

7. The hair dye composition of claim 1 which contains, in addition to the coupler of formula (I) another coupler selected from the group consisting of a meta-diphenol, a meta-aminophenol, a meta-phenylenediamine, a meta-acylaminophenol, a meta-ureidophenol, a meta-carbalkoxyaminophenol, α-naphthol, a β-keto compound and a pyrazolone.

8. The hair dye composition of claim 1 wherein said oxidation dye precursor of the para type is present in an amount ranging from 0.1 to 7 percent by weight based on the total weight of said composition.

9. The hair dye composition of claim 1 which also contains a dye precursor of the ortho type selected from the group consisting of an ortho-aminophenol, an ortho-phenylenediamine and an ortho-diphenol.

10. The hair dye composition of claim 1 which also contains a direct dye selected from the group consisting of an azo dye, an anthraquinone dye and a nitrobenzene dye.

11. The hair dye composition of claim 1 having a pH ranging from 8 to 11.

12. The hair dye composition of claim 1 having a pH ranging from 9 to 11.

13. The hair dye composition of claim 1 which also contains an organic solvent present in an amount ranging from 1 to 40 percent by weight based on the total weight of said composition, said organic solvent being selected from the group consisting of a lower alkanol, glycerol, a glycol, a glycol ether and a mixture thereof.

14. The hair dye composition of claim 1 which also contains at least one anionic, cationic, nonionic or amphoteric surfactant, or a mixture thereof, in an amount ranging from 0.5 to 40 percent by weight based on the total weight of said composition.

15. The hair dye composition of claim 1 which also includes at least one cosmetic adjuvant selected from a thickener, an antioxidant, a penetrating agent, a sequestering agent, a buffer, a perfume, an alkalinizing agent and a propellant.

16. A process for dyeing hair comprising
(a) admixing at the time of use the hair dye composition of claim 1 with an oxidizing solution in an amount effective to develop the oxidation dye precursor,
(b) applying the mixture obtained in step (a) to the hair,
(c) permitting said mixture to remain on the hair for a period of time ranging from 10 to 40 minutes,
(d) rinsing the hair,
(e) shampooing the hair,
(f) rinsing the shampooed hair with water, and
(g) drying the hair.

17. A process for dyeing hair comprising
(a) in a first stage, applying to the hair an oxidation precursor of the para type selected from the group consisting of a para-phenylenediamine, a para-aminophenol, a heterocyclic para compound and a mixture thereof,
(b) in a second stage, applying to the hair treated in said first stage at least one coupler compound having the formula

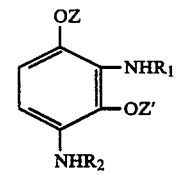

wherein
$R_1$ and $R_2$, each independently, represent hydrogen, alkyl having 1-4 carbon atoms, monohydroxyalkyl having 2-3 carbon atoms or polyhydroxyalkyl having 2-3 carbon atoms,
Z and Z', each independently, represent alkyl having 1-4 carbon atoms or hydroxyalkyl having 2-4 carbon atoms, with the proviso that, when $R_1$ and $R_2$ simultaneously represent hydrogen, Z and Z' do not simultaneously represent methyl, or
the acid addition salt thereof, together with an oxidizing agent, or alternatively
in a third stage, applying said oxidizing agent separately to said hair treated with said coupler compound of formula (I) in said second stage,
(c) permitting said oxidation precursor of the para type, said coupler compound and said oxidizing agent previously applied to the hair to remain on the hair for a period of time ranging from 10 to 40 minutes,
(d) rinsing the hair,
(e) shampooing the hair,
(f) rinsing the shampooed hair, and
(g) drying the hair.

* * * * *